(12) United States Patent
Bressau et al.

(10) Patent No.: US 12,366,494 B2
(45) Date of Patent: Jul. 22, 2025

(54) GEL-COUPLED PRESSURE SENSOR DEVICE WITH INTERFERENCE-INDEPENDENT CONTACT SIDE FOR CONNECTION TO AN INFUSION HOSE

(71) Applicant: B. Braun Melsungen AG, Melsungen (DE)

(72) Inventors: Ernst Bressau, Malsfeld (DE); Michael Kauba, Fuldabrueck (DE); Hans-Christian Moritzen, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 297 days.

(21) Appl. No.: 17/967,765

(22) Filed: Oct. 17, 2022

(65) Prior Publication Data

US 2023/0139653 A1 May 4, 2023

(30) Foreign Application Priority Data

Oct. 29, 2021 (DE) ...................... 10 2021 128 378.7

(51) Int. Cl.
*G01L 19/04* (2006.01)
*A61B 5/00* (2006.01)
(Continued)

(52) U.S. Cl.
CPC .......... *G01L 19/04* (2013.01); *G01L 19/0023* (2013.01); *A61B 5/6866* (2013.01);
(Continued)

(58) Field of Classification Search
CPC ... G01L 19/04; G01L 19/0023; G01L 9/0002; G01L 19/0038; G01L 11/00; A61B 5/6866; A61B 2562/0247; A61M 5/16854
See application file for complete search history.

(56) References Cited

U.S. PATENT DOCUMENTS 4,027,536 A 6/1977 Heggie
5,939,640 A 8/1999 Hauser
(Continued)

FOREIGN PATENT DOCUMENTS

DE 2647402 A1 4/1977
DE 19610828 C1 * 3/1997 ........... A61B 5/0215
(Continued)

OTHER PUBLICATIONS

Search Report received in German Application No. 10 2021 128 378.7 dated Jun. 20, 2022, with translation, 11 pages.
(Continued)

*Primary Examiner* — Peter J Macchiarolo
*Assistant Examiner* — John M Royston
(74) *Attorney, Agent, or Firm* — Christopher A. Rothe; CM Law

(57) ABSTRACT

A pressure sensor device for internal pressure monitoring in a hose, preferably an infusion hose, that is used for fluid transmission and that rests directly or indirectly on a pressure sensor housing. The hose is elastically deformable and connected via a contact side to a pressure transmission element located in the pressure sensor housing. The pressure transmission element transmits internal pressure changes absorbed via the contact side to a compressive force sensor for measurement. The contact side can have an elliptical shape, and the pressure transmission element can have a funnel-shaped extension, to make the pressure sensor device as robust as possible in terms of measurement accuracy, and independent of fluctuations in temperature and associated changes in material states.

19 Claims, 7 Drawing Sheets

(51) Int. Cl.
*A61M 5/168* (2006.01)
*G01L 9/00* (2006.01)
*G01L 11/00* (2006.01)
*G01L 19/00* (2006.01)

(52) U.S. Cl.
CPC .. *A61B 2562/0247* (2013.01); *A61M 5/16854* (2013.01); *G01L 9/0002* (2013.01); *G01L 11/00* (2013.01); *G01L 19/0038* (2013.01)

(56) References Cited

U.S. PATENT DOCUMENTS

| | | | |
|---|---|---|---|
| 6,070,469 A * | 6/2000 | Taniguchi | G01L 19/0038 |
| | | | 73/715 |
| 6,148,673 A * | 11/2000 | Brown | G01L 19/141 |
| | | | 257/676 |
| 6,272,930 B1 | 8/2001 | Crozafon et al. | |
| 6,889,556 B2 | 5/2005 | Steger | |
| 2003/0217602 A1 | 11/2003 | Steger | |
| 2014/0033814 A1 * | 2/2014 | Wen | G01L 19/145 |
| | | | 257/419 |

FOREIGN PATENT DOCUMENTS

| | | |
|---|---|---|
| DE | 29602065 U1 | 3/1997 |
| DE | 20206474 U1 | 9/2003 |
| EP | 0594836 B1 | 5/1997 |
| EP | 0897528 B1 | 2/1999 |
| EP | 1269145 B1 | 4/2009 |
| EP | 1357372 B1 | 1/2014 |

OTHER PUBLICATIONS

Search Report received in European Application No. 22200264.4-1001 dated Mar. 21, 2023, with translation, 14 pages.

* cited by examiner

GEL-COUPLED PRESSURE SENSOR DEVICE WITH INTERFERENCE-INDEPENDENT CONTACT SIDE FOR CONNECTION TO AN INFUSION HOSE

CROSS-REFERENCE TO RELATED APPLICATIONS

This application claims priority under 35 U.S.C. § 119 to German Patent Application No. 10 2021 128 378.7, filed Oct. 29, 2021, the contents of which are incorporated by reference herein in their entirety.

FIELD

The present disclosure relates to a gel-coupled pressure sensor device, and in particular to a gel-coupled pressure sensor device that can be mounted on hoses, in particular medical infusion hoses, for inner hose pressure detection substantially free of measurement fluctuations.

BACKGROUND

In medical technology, flexible hoses are used, for example, to supply fluid to a patient by infusion, to remove fluid from a patient, or to transfer fluid between devices or appliances. However, such hoses are also used, for example, for blood treatment machines, heart-lung machines and similar intensive care devices. Here, there is a need to detect partial or complete occlusion of the flexible hose, such as occurs when the hose kinks. In addition, depending on the infusion parameters set, it is necessary to monitor the internal pressure of the infusion hose and to regulate it according to the set parameters.

Pressure sensor devices are known from EP 1 269 145 B1, EP 0 897 528 B1, EP 0 594 836 B1 and EP 1 357 372 B1, generally consisting of, among other things, a pressure sensor housing in which a pressure receiving and pressure transmission medium or pressure transmission element is arranged and a compressive force sensor which is in contact with the pressure transmission element. In particular, the pressure transmission element is configured to come into contact with the infusion hose for detection of a radial hose expansion due to a current internal pressure of the hose and to allow a pressure transmission from the infusion hose to the compressive force sensor located in the pressure sensor housing as precisely and sensitively as possible in order to measure the internal pressure of the infusion hose.

Gel has been recommended as a possible suitable medium for pressure transmission, which is inserted/filled in a chamber of a sensor housing and may have a contact portion projecting from the sensor housing, against which the gel rests on a hose. The gel/gel element/gel pad/gel cushion, or gel body thus forms a pressure transmission element. However, in an area of application with active medical devices such as infusion pumps and/or dialysis devices, particularly high demands are placed on the accuracy of the monitored parameters, such as in particular internal pressures in infusion hoses.

However, fluctuations in temperature and the associated changes in the dimensions and material states of individual functional elements, in particular the gel-based pressure transmission elements, may lead to large measurement fluctuations in pressure sensor systems. In other words, fluctuations in temperature have been shown to lead to measurement fluctuations, wherein it has not yet been clear which material or geometric parameters are influenced by said fluctuations in temperature that are largely responsible for the measurement fluctuations.

The prior art does not yet offer any gel-coupled pressure sensor devices that meet the high requirements of infusion pumps and dialysis devices (or other medical applications for measuring blood/fluid pressure in a hose) in a stable manner and are robust against temperature-dependent interferences. The prior art to date therefore has the disadvantage that measurement fluctuations caused by temperature influences cannot be sufficiently compensated for in order to be able to carry out reliable and highly precise measurements via gel-coupled pressure sensor devices.

SUMMARY

Accordingly, it is the objective of the present disclosure to provide a pressure sensor device that is or can be connected to an infusion hose via gel-based coupling from the pressure transmission element, preferably a gel body, and can provide continuously accurate measurements over as wide a temperature range as possible.

In the search for a solution to this technical object, empirical tests have shown that especially the contact-side geometry of the pressure transmission element, on which the hose is placed, and on which a contact surface forms between the pressure transmission element and the hose, has a great influence on the measurement accuracy in the pressure sensor device, and that the contact surface forming on the contact side of the pressure transmission element can change considerably with changes in temperature.

Further experiments have also shown that certain contact-side geometries of pressure transmission elements form contact surfaces to the hose that change less under the influence of temperature than the contact surfaces of other contact-side geometries. In other words, the contact-side geometry has a great influence on how much the forming contact surface between contact side and hose changes under fluctuations in temperature and thus triggers the measurement fluctuation accordingly.

It was concluded that the less the contact surface changes with temperature changes, the more precisely the compressive force sensor can deliver output voltages corresponding to the pressures actually prevailing in the hose. The observations made in the experiments can be plausibly justified using the formula for calculating pressure $P=F/A$. If the contact surface forming between the contact side and the hose remains almost constant, the changes in pressure can be determined with constant precision via the measured force.

The experiments carried out for the invention proved that the measuring accuracies of the pressure sensor device were higher in particular when the contact surface of the contact-side geometry of the pressure transmission element in contact with the hose changed little with changes in temperature.

However, the known contact-side geometries from the prior art, such as circular or tear-shaped along the direction of the hose as published in EP 1 269 145 B1, did not lead to satisfactory measurement results of a gel-based pressure sensor device at fluctuations in temperature.

Accordingly, the concrete technical problem for solving the stated object was to create a contact-side geometry which, in conjunction with the remaining spatial pressure transmission element configuration, can form a contact surface to the hose which remains as constant as possible under fluctuations in temperature.

According to a first aspect of the invention, the pressure sensor device comprises a gel mounted in a pressure sensor housing as a pressure receiving and pressure transmission element, which has, on a pressure inlet portion projecting freely from the pressure sensor housing, an abutment or contact side defining an insertion direction for a fluid pressure hose inserted or insertable into the pressure sensor device and, starting from the contact side, extends through the pressure sensor housing, preferably configuring a funnel shape or stepwise constriction shape, all the way to a compressive force sensor. The pressure inlet portion, in particular the contact side, has a shape that is symmetrical both to its longitudinal axis and to its transverse axis, and the longitudinal extent of the contact side parallel to the insertion direction is greater than in the transverse direction thereto.

A geometric shape with the proportion ratios of the aforementioned contact side, which is larger in the longitudinal direction of the hose than in the circumferential direction and is symmetrical in both its longitudinal and transverse axes, offers the advantage that it can compensate for associated material conditions even in the event of significant fluctuations in temperature of the environment of the pressure sensor device, while hardly changing its overall surface. At the same time, changes in pressure occurring in the hose are still passed on unaltered to the pressure transmission element and to the compressive force sensor connected to it.

The axial symmetric shape of the contact side extending along the longitudinal axis of the hose ensures an evenly distributed pressure transfer of the hose to both halves of the contact side. The axial symmetry to the transverse axis of the contact side also contributes to uniform pressure distribution along the longitudinal direction of the contact surface and prevents unevenly distributed tension states that can be caused by an asymmetrical surface distribution.

Furthermore, in accordance with a further aspect of the invention, it is preferably provided that the pressure inlet portion, in particular the contact side, tapers in its longitudinal extension towards its respective ends. This further improves the aforementioned effect of higher temperature fluctuation resistance.

In accordance with a further aspect of the invention, the pressure inlet portion, in particular the contact surface, may taper to a point in its longitudinal extent or may have the shape of a rhombus.

Furthermore, the contact side may form an outer line without corners.

A contact side without corners offers the advantage that tension states between the hose and the pressure transmission element are distributed more evenly by the rounded shape of the contact side than is the case in corner areas with pointed or respectively angular transitions, so that the more uniform tension distribution also results in less locally concentrated distortion of the contact side and associated measurement falsifications.

Furthermore, the contact side may have almost the shape of a rectangle, wherein transitions between the narrow side and the long side are arc-shaped.

An almost rectangular contact surface offers the advantage of creating as much contact area as possible along a strip, and at the same time, transition areas between narrow and long sides configured as curves or radii offer the possibility of omitting sharp or pointed corners, which may lead to locally concentrated tension states and thus to distortions and changes or falsifications in the measurement results.

Furthermore, the geometry of the contact side may taper continuously from its transverse axis to its ends.

In a further aspect, the geometry of the contact side may have the shape of an ellipse whose main or longitudinal axis runs parallel to the longitudinal axis of the hose.

Experiments have shown that the geometry of an ellipse in particular is extremely robust against temperature-induced surface changes and is therefore particularly preferred. In summary and in other words, the invention of a first, particularly preferred embodiment is based on an elliptical geometry of the gel surface or gel contact side of a gel-coupled pressure sensor, which leads to an optimized hose-gel-sensor coupling in order to reduce the environmental dependence of the performance parameters, in particular as a result of fluctuations in temperature.

The hose-sensor coupling is crucial for the performance of the sensor, since existing sensors exhibit e.g. temperature dependencies, which can be traced back to unstable contact sides and contact surfaces as well as boundary surfaces. In the prior art, however, the shape of the contact side and of the contact surface being formed is not considered in terms of flexibility/constant performance over the temperature range. Therefore, to date, there is no gel-coupled sensor that meets the requirements for high performance stability in active medical devices, such as infusion pumps and/or dialysis machines.

Now, according to the present disclosure, in order to be able to reduce the temperature dependence of the pressure sensor device, it is essential to identify the optimal shape or geometry of the contact surface between the hose and the gel or gel pad, respectively, to ensure a constant sensor output voltage due to an optimal and stable contact surface under different environmental conditions.

Due to temperature influences, the height of the gel of a gel-coupled pressure sensor device changes. Due to the change in height, the contact side and contact surface between gel and hose is not constant. However, as explained above, the contact surface of the hose has a direct influence on the output level of a gel-coupled compressive force sensor. An elongated (with respect to the X- and Y-axis) axisymmetric side/surface shape in the longitudinal direction of the hose, and in particular an elliptical shape or geometry of the gel surface of a gel-coupled pressure sensor device, unexpectedly leads to an optimized hose-gel-sensor coupling in order to reduce environmental dependencies (e.g. temperature drift) of the sensor output voltage. The resulting lower tolerances and smaller output fluctuations open up new fields of application, e.g. for infusion pumps and dialysis devices, for this type of sensor.

In a preferred arrangement of hose to pressure transmission element, the hose lies exactly on the main axis of the elliptical contact side. The coupling surface or contact surface between pressure transmission element and hose is and remains thereby constant—even if the gel material in the pressure transmission element contracts or expands due to temperature changes.

For sealing and as a protective measure, a silicone cap and further separating materials, preferably in the form of membranes, can additionally be used in the pressure sensor device between the gel of the pressure transmission element and the hose, which due to its comparatively thin wall thickness or material thickness has no influence on the effects according to the disclosure.

In a particularly preferred aspect of the invention, the pressure sensor device may have an elliptical contact side, wherein the cross-section of the pressure transmission element below the pressure inlet portion decreases in a funnel-shaped, preferably monotonically decreasing manner in the direction of the compressive force sensor.

Particularly in combination, the elliptical contact side and the pressure transmission element with funnel-shaped cross-section complement each other. This is because the elliptical contact side stably maintains its contact surface forming to the hose under changes in temperature, while the funnel-shaped cross-section is less affected by fluctuations in temperature due to the reduced gel volume in the pressure transmission element and at the same time transmits the forces introduced from the contact side to the compressive force sensor concentrated on a smaller cross-section.

The combination of these two constructive features, namely the elliptical contact side and the funnel-shaped cross-section, increases both the measurement reliability and the measurement accuracy and measurement sensitivity of the pressure sensor. The effects of the two constructive features thus act synergistically on each other and reduce the overall temperature dependency of the pressure sensor device.

BRIEF DESCRIPTION OF THE DRAWINGS

The present disclosure is explained in more detail below based on preferred embodiments with reference to the accompanying figures.

DETAILED DESCRIPTION

The following describes configuration examples of the present disclosure based on the accompanying figures. Identical elements are indicated by the same reference signs. Features of the individual configuration examples are interchangeable with each other.

Figure 1:
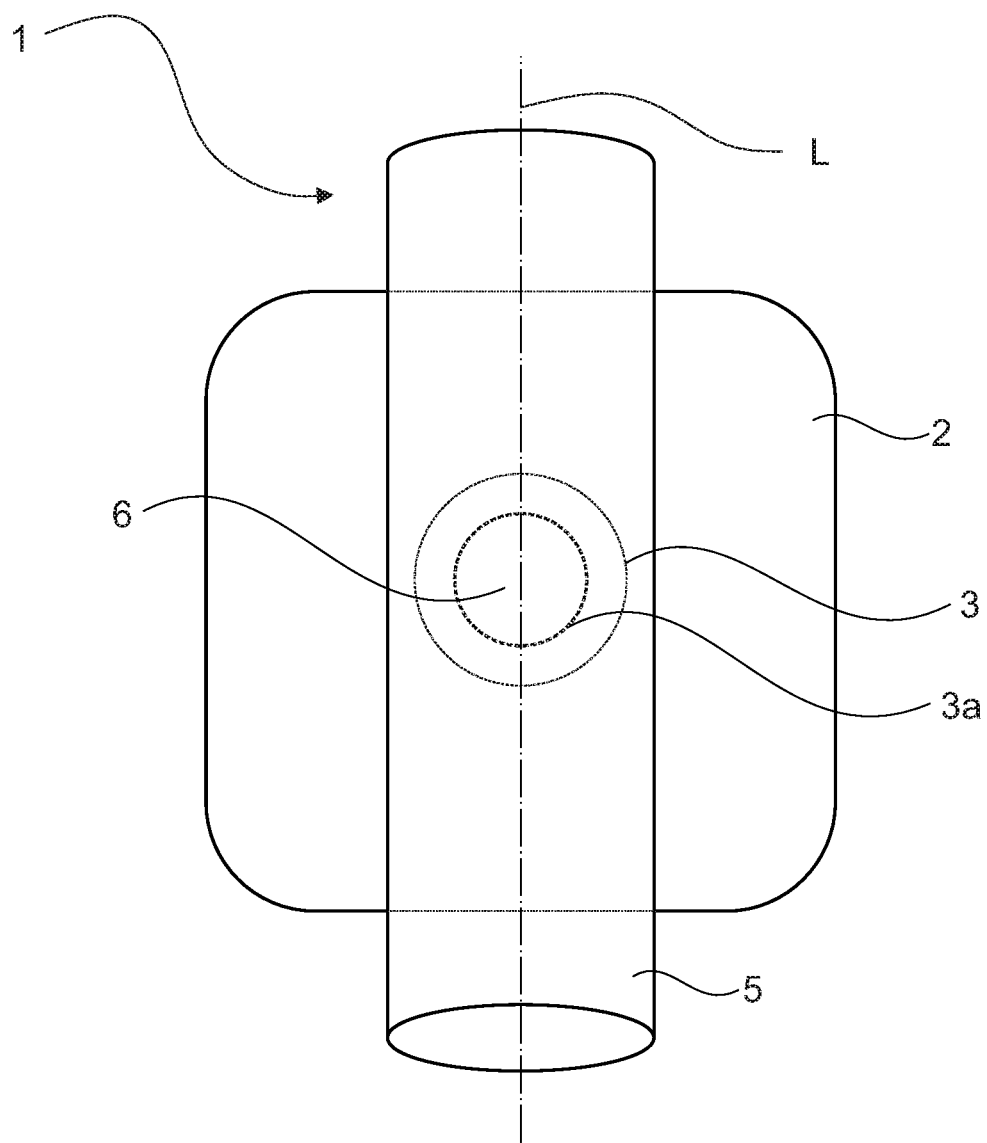
FIG. 1 is a top view of a pressure sensor unit with a contact-side geometry known from the prior art.

FIG. 1 shows a pressure sensor device 1 with a pressure sensor housing 2 and a contact side 3 of a pressure transmission element 4. A fluid pressure hose 5, hereinafter referred to as hose, is placed on the contact side 3 of the pressure transmission element 4. The geometry of the contact side 3 corresponds to known application geometries from the prior art.

Under favorable temperature conditions, a contact surface 3a is formed between the contact side 3 of the pressure transmission element 4 and the hose 5 over the entire area of the contact side 3, but in the event of fluctuations in temperature, the contact surface 3a formed between the pressure transmission element 4 and the hose 5 varies greatly, so that the contact surface 3a may be significantly smaller than the contact side 3, as shown in FIG. 1. These unwanted fluctuations in the surface area of the contact surface 3a on the contact side 3 of the pressure transmission element also result in strong fluctuations in the measuring accuracy of the pressure sensor 1 in the prior art.

Figure 2:
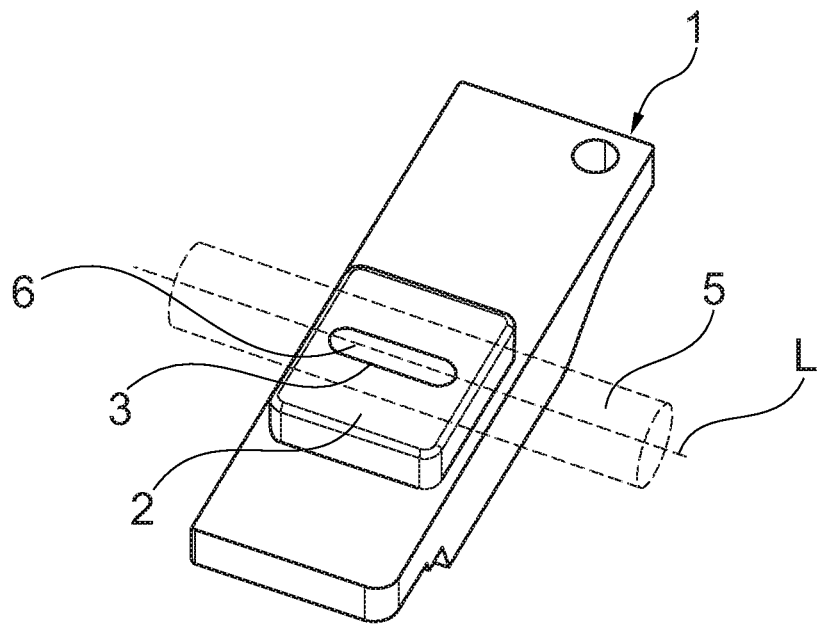
FIG. 2 is a perspective view of the pressure sensor device according to a first embodiment of the present disclosure.

FIG. 2 shows a perspective view of a pressure sensor 1 according to the invention, which solves the problem described in FIG. 1. The pressure sensor 1 has a pressure sensor housing 2 with a contact side 3 of a pressure transmission element 4 shown in more detail in FIG. 3, on which a hose 5, preferably an infusion hose 5, rests. Particularly noteworthy is the elliptical geometry of the contact side 3, which is extremely stable in terms of surface area with respect to fluctuations in temperature, so that the contact surface 3a forming between the pressure transmission element 4 and the hose 5 is constant and corresponds virtually to the surface area of the contact side 3.

Figure 3:
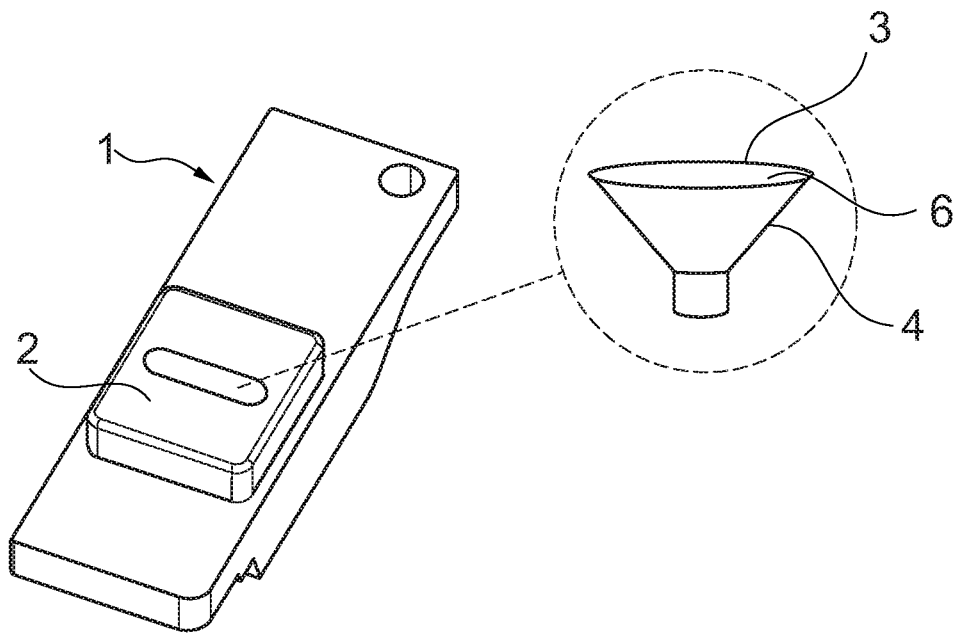
FIG. 3 is a perspective view of the pressure sensor device according to the first embodiment with a detailed view of the pressure transmission element.
Figure 5:
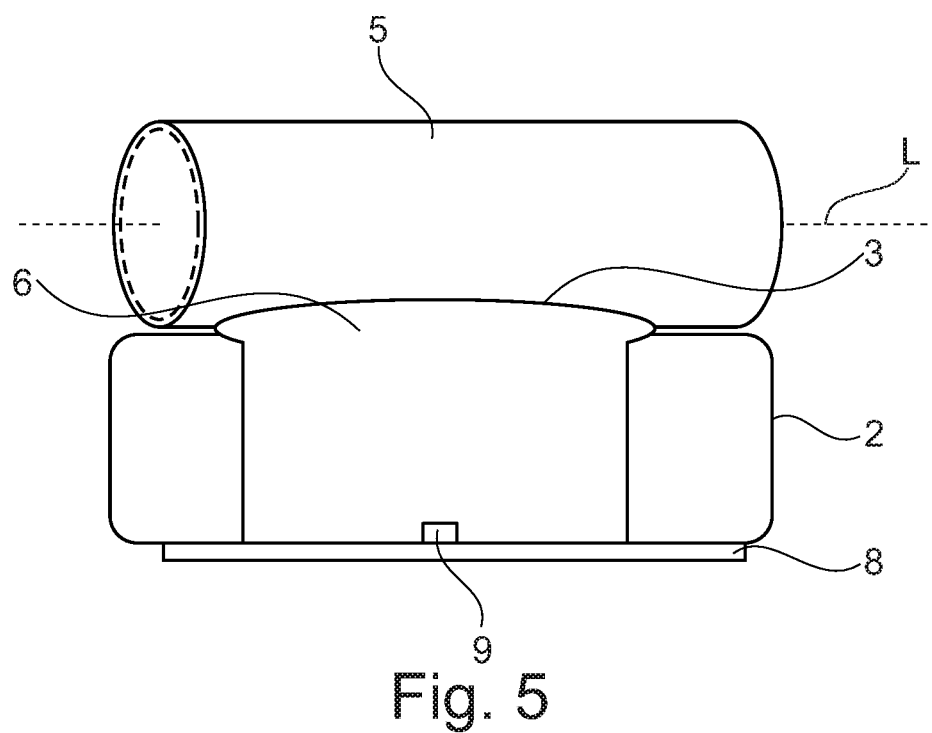
FIG. 5 is a partially sectional view of a second embodiment with a cushion-like pressure inlet portion of the pressure transmission element, wherein the pressure transmission element runs below the pressure inlet portion in a cylindrical shape towards the compressive force sensor.
Figure 7:
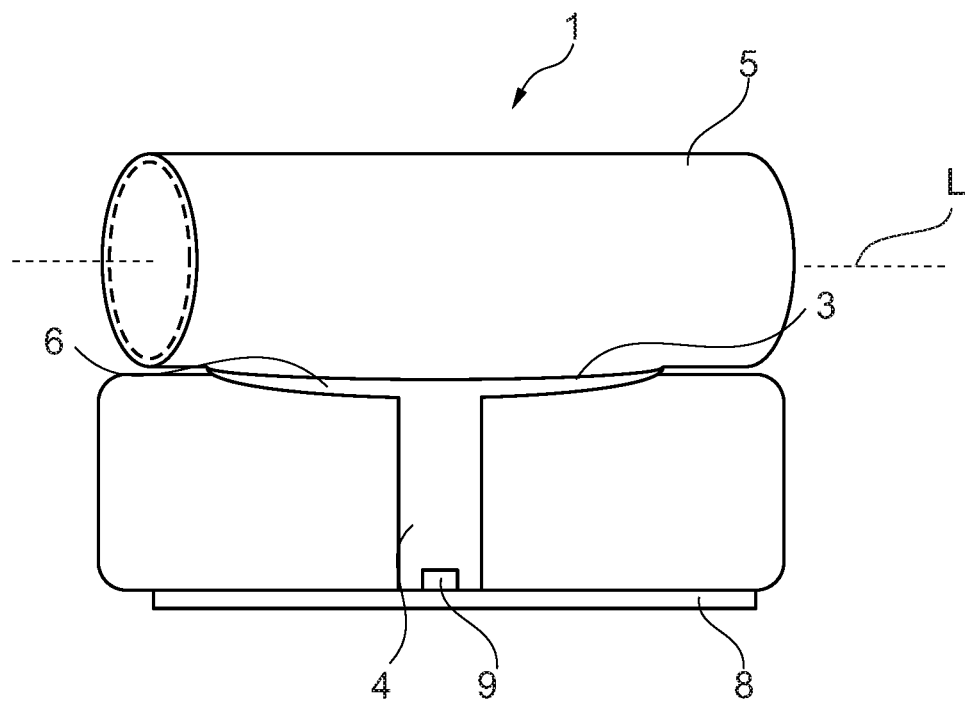
FIG. 7 is a partially sectional view of the pressure sensor device according to a third embodiment having a pressure transmission element with stepwise constriction shape.

In FIG. 3, the pressure sensor 1 according to the invention is shown without the hose 5 and with a detailed view of the funnel-shaped pressure transmission element 4 detached from the pressure sensor housing 2. Depending on the embodiment, the funnel shape may be formed in different ways and may, for example, also have a stepwise constriction shape as shown in FIG. 7. Furthermore, the pressure inlet portion 6 of the pressure transmission element 4 facing the hose may be convex or even concave in the direction of the hose 5, as shown in FIG. 5 and FIG. 7.

Figure 4:
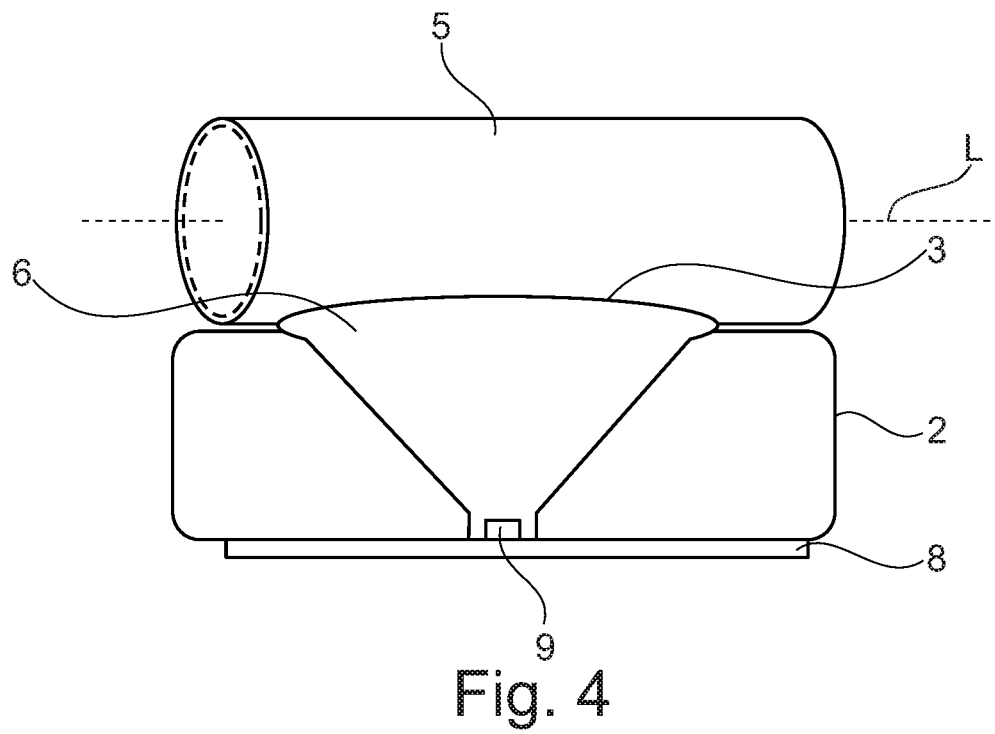
FIG. 4 is a partially sectional view of the pressure sensor device according to the first embodiment with a cushion-like pressure inlet portion of the pressure transmission element tapering monotonically in a funnel shape towards the compressive force sensor.

In FIG. 4, the pressure sensor 1 of the first embodiment is shown in a partially sectional view along the longitudinal axis L of the hose 5, which itself is not cut. The hose 5 is made of a flexible material that is elastic and thus has resilience. The cross-section of the hose 5 is round. The hose 5 contains a liquid, for example an infusion solution, which is supplied to a patient. As can be seen from FIG. 4, the hose 5 rests only indirectly on the pressure sensor housing 2 and rests directly on a cushion-like, freely projecting pressure inlet portion 6 of the pressure transmission element 4. The pressure transmission element 4 extends from a contact side 3 on the pressure inlet portion 6, via which the hose 5 rests on the pressure transmission element 4, through the pressure sensor housing 2 in a funnel shape with an elliptical base area and is supported on a printed circuit board 8 and a compressive force sensor 9 arranged thereon.

The compressive force sensor 9 may, for example, have strain gauges connected in a bridge circuit or a piezo compressive force sensor. Both the strain gauges and the piezo compressive force sensor generate an electrical signal that is proportional to the force F acting on the compressive force sensor 9.

If changes in pressure occur in the hose 5, for example due to changes in the composition of the fluid or due to kinking of the hose 5, these are picked up via the contact side 3 of the pressure transmission element 4 and are transmitted via the gel-like force transmission means 4 to the compressive force sensor 9, which emits an electrical, measurable signal proportional to the applied force.

The pressure transmission element 4 is preferably made of incompressible gel, which is particularly suitable for transmitting force between the hose 5 and the compressive force sensor 9. However, fluctuations in temperature may have a significant effect on the volume of the pressure transmission element 4, so that the height of the gel in the pressure transmission element 4 may change. Due to the change in height, the contact side 3 and contact surface 3a between the gel and the hose is not constant in geometries previously used in the prior art.

Due to the elliptical coupling surface 3 or contact side 3 according to the invention, the contact surface 3a forming between contact side 3 and hose 5 remains constant, even if the gel material contracts or expands due to changes in temperature. This makes it possible to achieve precise measurement results that meet the high standards for infusion and dialysis applications with regard to measurement accuracy, even under varying temperature influences.

In particular, the funnel-shaped, monotonously decreasing cross-section of the pressure transmission element 4 of the first embodiment of the pressure sensor 1 allows, on the one hand, the configuration of a relatively large contact side 3 at the pressure inlet portion 6 towards the hose 5 and, on the other hand, a clear cross-sectional tapering in the direction of the compressive force sensor 9, so that the support area of the pressure transmission element 4 around the compressive force sensor 9 is kept as small as possible. The funnel shape of the cross-section of the pressure transmission element 4 thus allows changes in pressure to be detected in the hose 5 over a relatively large area, and these changes can be transmitted to the compressive force sensor 9 in as concentrated a manner as possible due to the tapering cross-section of the funnel shape, without a significant portion of the transmitted forces being introduced into the peripheral area around the compressive force sensor 9. The funnel-shaped cross-section of the pressure transmission element 4 thus helps to ensure that the compressive force sensor 9 can measure highly sensitively.

Another advantageous effect of the funnel-shaped cross-section is that gel volume can be saved in the pressure transmission element 4 compared to a pressure transmission element 4 with a constant cross-section from contact side 3 to compressive force sensor 9. The reduction in volume of the temperature-dependent gel in the pressure transmission element 4 thus reduces the sensitivity to temperature changes of the pressure sensor 1 and increases measurement reliability.

Overall, it can be said that the positive effects of the elliptical contact side 3 and of the funnel-shaped cross-section of the pressure transmission element 4 complement each other. The elliptical contact side 3 stably maintains its contact surface 3a formed to the hose 5 under changes in temperature, while the funnel-shaped cross-section is less affected by fluctuations in temperature due to reduced gel volume in the pressure transmission element 4 and at the same time transmits the forces introduced from the contact side 3 to the compressive force sensor in a concentrated manner.

In FIG. 5, the pressure sensor unit 1 of a second embodiment is shown in a partially sectional view along the longitudinal axis L of the hose 5, which itself is not cut. As can be seen from FIG. 5, the hose 5 rests only indirectly on the pressure sensor housing 2 and rests directly on a cushion-like, freely projecting pressure inlet portion 6 of the pressure transmission element 4. The pressure transmission element 4 extends below the cushion-like pressure inlet portion 6 with a constant cylindrical cross-section with an elliptical basic shape (seen from above) through to the pressure sensor housing 2 and is supported on a printed circuit board 8 and on a compressive force sensor 9 arranged thereon.

Figure 6:
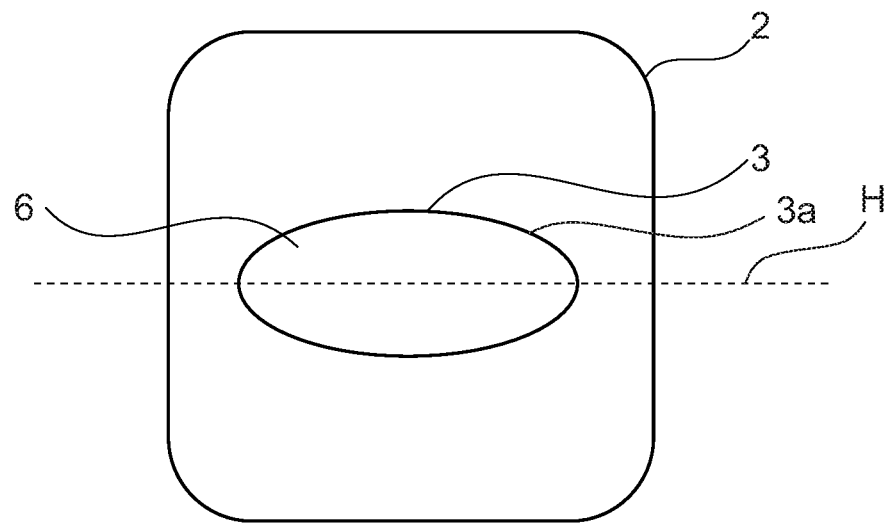
FIG. 6 is a top view of the support body and of the contact side and contact surface of the pressure transmission element of the pressure sensor device.

In FIG. 6, the cross-section of the contact side 3 is shown in a top view against the background of the pressure sensor housing 2. The main axis H of the ellipse formed by the contact side 3 is parallel to the longitudinal axis L (not shown in FIG. 6) of the hose 5, so that changes in pressure in the hose 5 are distributed evenly on both sides of the main axis H of the ellipse of the contact side 3. The contact side 3 has almost the same area as the contact surface 3a forming between pressure transmission element 4 and hose 5, as shown in FIG. 6.

In FIG. 7, the pressure sensor unit 1 of a second embodiment is shown in a partially sectional view along the longitudinal axis L of the hose 5, which itself is not cut. The pressure transmission element 4 is configured in a funnel-like, stepwise constriction shape with significantly reduced gel volume compared to the first embodiment.

The pressure inlet portion 6 of the pressure transmission means 4 is concavely curved into the pressure sensor housing 2 and the cross-section of the pressure transmission element 4 below the contact side 3 is narrow-cylindrical towards the compressive force sensor 9. The reduction in volume of the gel in the pressure transmission element 4 represents a further possibility of reducing the temperature influence on the temperature-dependent gel volume of the pressure transmission element 4 and of being able to control or compensate for associated changes in the material states more effectively. Furthermore, the comparatively narrow cylindrical cross-section reduces the support area of the gel around the compressive force sensor 9, which means that the force transmission is more concentrated on the compressive force sensor 9, so that the pressure sensor sensitivity can be increased.

Figure 8:
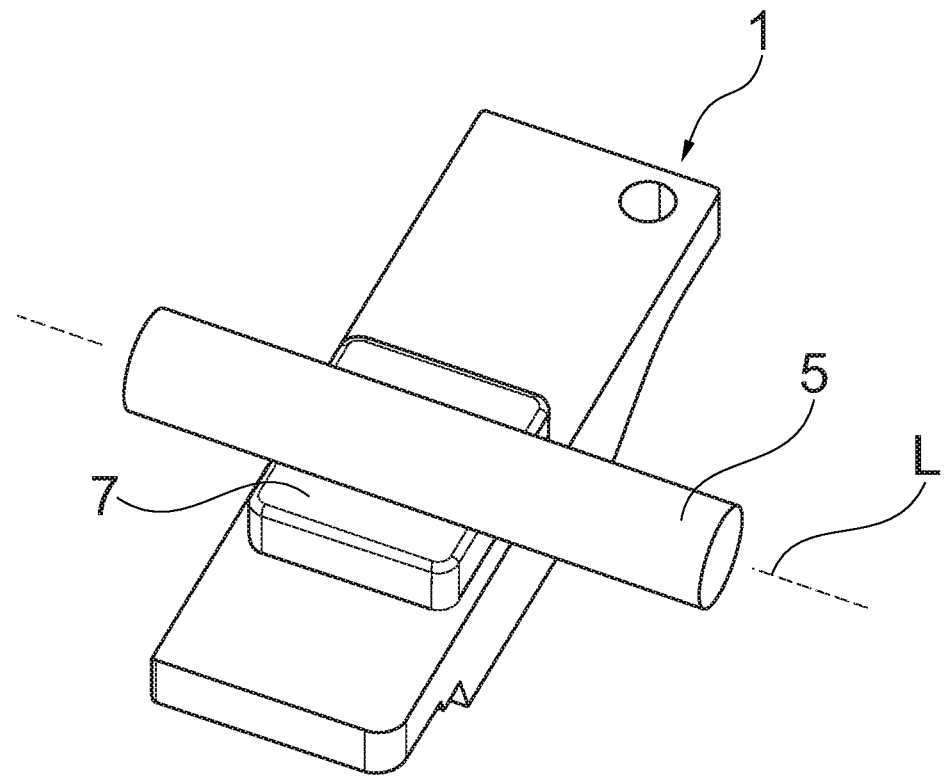
FIG. 8 is a perspective view of the pressure sensor device according to a fourth embodiment.

FIG. 8 shows a fourth embodiment of the pressure sensor device 1, in which the pressure sensor housing 2 as well as the pressure transmission element 4 and the compressive force sensor 9 are fluid-tight and protected from contamination by a silicone cap 7.

Figure 9:
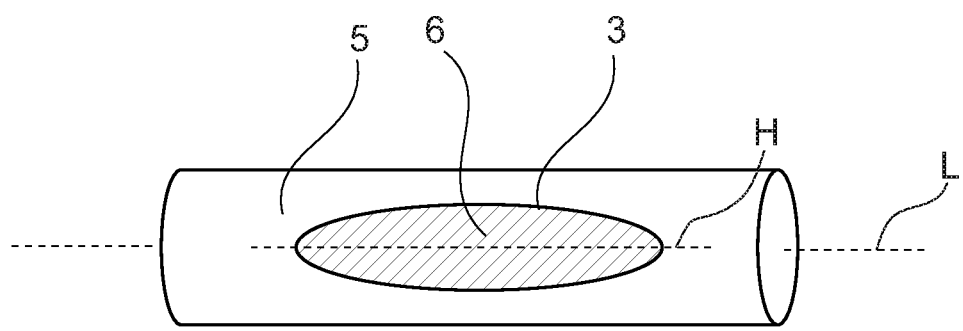
FIG. 9 is a perspective view of the hose of the pressure sensor device with highlighted contact side.

As can be seen in FIG. 9, the hose 5 is also placed on the silicone cap 7 with an elliptical contact side 3.

Figure 10:
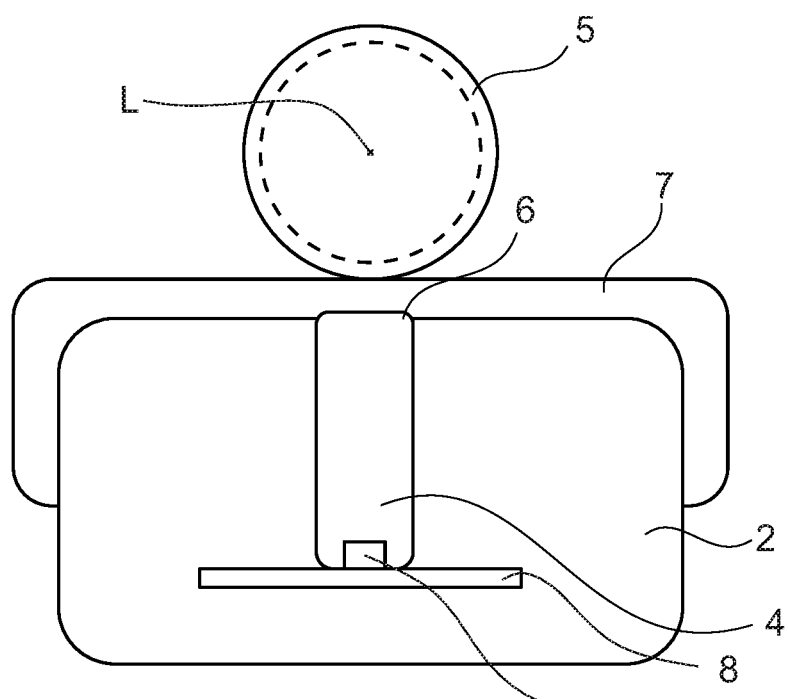
FIG. 10 is a sectional view perpendicular to the longitudinal axis of the hose of the pressure sensor device according to the fourth embodiment.
Figure 11:
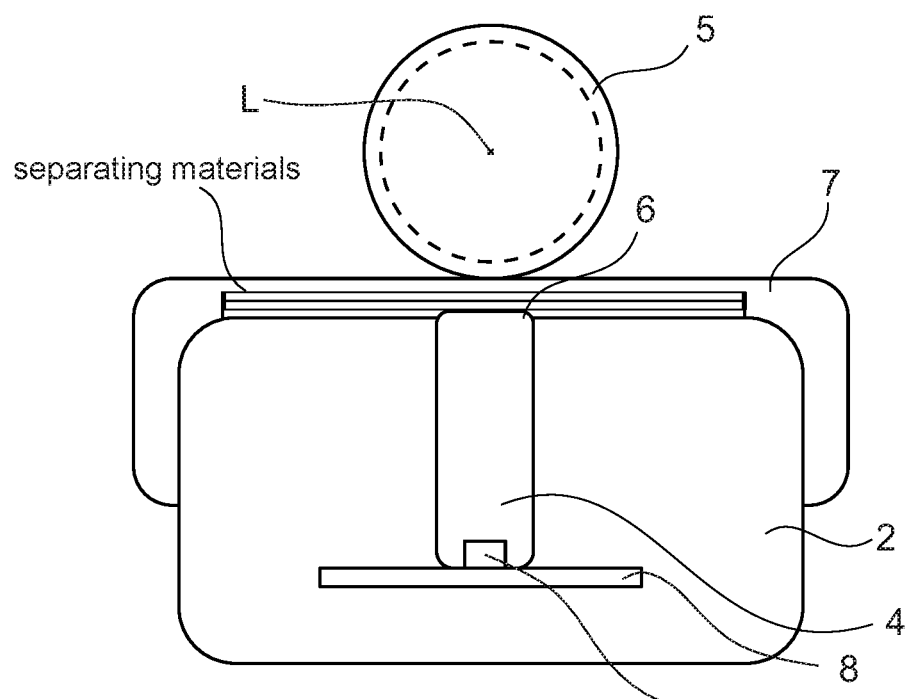
FIG. 11 is a sectional view perpendicular to the longitudinal axis of the hose of the pressure sensor device according to FIG. 10 with separating materials arranged between the pressure absorption and the pressure transmission element and the fluid pressure hose.

In FIG. 10, the pressure sensor device 1 of the fourth embodiment is shown in section perpendicular to the longitudinal axis L of the hose 5. In contrast to the first, second and third embodiments of the pressure sensor device 1, in the fourth embodiment the hose 5 is only placed indirectly on the pressure transmission element 4 and is placed directly on the silicone cap 7. The changes in pressure occurring in the hose 5 are transmitted via the elastic silicone cap to the pressure transmission element 4 connected underneath and extending through the pressure sensor housing 2 and are transmitted to the compressive force sensor 9 located on the printed circuit board 8. The mode of operation of the pressure sensor device 1 of the third embodiment is identical to the mode of operation of the pressure sensor device 1 of the first and second embodiment, except for the additional covering and force transmission by the silicone cap 7.

What is claimed:

1. A pressure sensor device comprising:
a pressure sensor housing;
a gel mounted in the pressure sensor housing so as to form a pressure absorption and pressure transmission element; and
a compressive force sensor,
the pressure absorption and pressure transmission element comprising a pressure inlet portion located at a side of the pressure sensor housing,
the pressure absorption and pressure transmission element further comprising a contact side extending from the pressure inlet portion to project freely from the side of the pressure sensor housing,
the contact side defining an insertion direction for a fluid pressure hose inserted or insertable into the pressure sensor device,
the pressure absorption and pressure transmission element extending in a depth direction from the contact side, away from the side of the pressure sensor housing, and into the pressure sensor housing to the compressive force sensor,
the pressure inlet portion defining a longitudinal axis and a transverse axis,
the pressure inlet portion having a shape that is symmetrical relative to the longitudinal axis and to the transverse axis,
the pressure inlet portion further defining a longitudinal extent parallel to the insertion direction and perpendicular to the depth direction and a longitudinal extent transverse to the insertion direction and perpendicular to the depth direction, and,
the longitudinal extent parallel to the insertion direction being greater than the longitudinal extent transverse to the insertion direction.

2. The pressure sensor device according to claim 1, wherein the pressure absorption and pressure transmission element comprise a funnel or a stepwise constriction in shape along the depth direction to the compressive force sensor.

3. The pressure sensor device according to claim 1,
wherein the contact side has a symmetrical shape relative to the longitudinal axis and to the transverse axis,
wherein the contact side defines a contact side longitudinal extent parallel to the insertion direction and perpendicular to the depth direction and a contact side longitudinal extent transverse to the insertion direction and perpendicular to the depth direction, and
wherein the contact side longitudinal extent parallel to the insertion direction is greater than the contact side longitudinal extent transverse to the insertion direction.

4. The pressure sensor device according to claim 1, wherein the pressure inlet portion tapers towards its ends, as viewed along the depth direction.

5. The pressure sensor device according to claim 1, wherein the pressure inlet portion and the contact side taper toward their respective ends, as viewed along the depth direction.

6. The pressure sensor device according to claim 1, wherein the shape of the pressure inlet portion tapers to a point or is a rhombus, as viewed along the depth direction.

7. The pressure sensor device according to claim 1, wherein the pressure inlet portion and the contact side taper to a point or have a rhombus shape, as viewed along the depth direction.

8. The pressure sensor device according to claim 1, wherein the contact side forms an outer line without corners, as viewed along the depth direction.

9. The pressure sensor device according to claim 1, wherein the contact side comprises two long sides joined by arc-shaped ends, as viewed along the depth direction.

10. The pressure sensor device according to claim 1, wherein the contact side has a transverse axis and two ends, the contact side having a geometry that tapers continuously from the transverse axis toward each of the two ends, as viewed along the depth direction.

11. The pressure sensor device according to claim 1, wherein the contact side has an elliptical shape, as viewed along the depth direction.

12. The pressure sensor device according to claim 11, wherein the contact side defines a main or longitudinal axis oriented to be parallel to a longitudinal axis of the fluid pressure hose when the fluid pressure hose is inserted into the pressure sensor device.

13. The pressure sensor device according to claim 1, further comprising a silicone cap configured to be between the pressure absorption and pressure transmission element and the fluid pressure hose when the fluid pressure hose is inserted into the pressure sensor device, the silicone cap for sealing and protecting the pressure sensor housing.

14. The pressure sensor device according to claim 13, further comprising separating materials arranged between the pressure absorption and pressure transmission element and the fluid pressure hose for sealing and protecting the pressure sensor housing.

15. The pressure sensor device according to claim 14, wherein the separating materials are formed as membranes.

16. The pressure sensor device according to claim 11, wherein the pressure absorption and pressure transmission element has a cross-section extending in the depth direction below the pressure inlet portion that tapers in a funnel-shaped manner toward the compressive force sensor.

17. The pressure sensor device according to claim 16, wherein the cross-section extending in the depth direction below the pressure inlet portion tapers in a funnel shaped, monotonically decreasing manner toward the compressive force sensor.

18. A pressure sensor device comprising:
a pressure sensor housing;
a gel mounted in the pressure sensor housing so as to form a pressure absorption and pressure transmission element; and
a compressive force sensor,
the pressure absorption and pressure transmission element comprising a pressure inlet portion,
the pressure absorption and pressure transmission element further comprising a contact side projecting freely from the pressure sensor housing,
the contact side defining an insertion direction for a fluid pressure hose inserted or insertable into the pressure sensor device,
the pressure absorption and pressure transmission element extending from the contact side through the pressure sensor housing to the compressive force sensor,
the pressure inlet portion defining a longitudinal axis and a transverse axis,
the pressure inlet portion having a shape that is symmetrical relative to the longitudinal axis and to the transverse axis,
the pressure inlet portion further defining a longitudinal extent parallel to the insertion direction and a longitudinal extent transverse to the insertion direction, and the longitudinal extent parallel to the insertion direction being greater than the longitudinal extent transverse to the insertion direction, wherein the pressure inlet portion tapers towards its ends.

19. A pressure sensor device comprising:

a pressure sensor housing;

a gel mounted in the pressure sensor housing so as to form a pressure absorption and pressure transmission element; and a compressive force sensor, the pressure absorption and pressure transmission element comprising a pressure inlet portion, the pressure absorption and pressure transmission element further comprising a contact side projecting freely from the pressure sensor housing, the contact side defining an insertion direction for a fluid pressure hose inserted or insertable into the pressure sensor device, the pressure absorption and pressure transmission element extending from the contact side through the pressure sensor housing to the compressive force sensor, the pressure inlet portion defining a longitudinal axis and a transverse axis, the pressure inlet portion having a shape that is symmetrical relative to the longitudinal axis and to the transverse axis, the pressure inlet portion further defining a longitudinal extent parallel to the insertion direction and a longitudinal extent transverse to the insertion direction, the longitudinal extent parallel to the insertion direction being greater than the longitudinal extent transverse to the insertion direction, wherein the contact side has an elliptical shape, and wherein the pressure absorption and pressure transmission element has a cross-section below the pressure inlet portion that tapers in a funnel-shaped manner toward the compressive force sensor.

\* \* \* \* \*